(12) United States Patent
Harris et al.

(10) Patent No.: US 11,591,659 B2
(45) Date of Patent: Feb. 28, 2023

(54) **COMPOSITIONS AND METHODS FOR DETECTION OF *MYCOPLASMA GENITALIUM***

(71) Applicant: Roche Molecular Systems, Inc., Pleasanton, CA (US)

(72) Inventors: Jody Harris, Lafayette, CA (US); Kalyani Mangipudi, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 341 days.

(21) Appl. No.: 16/800,938

(22) Filed: Feb. 25, 2020

(65) Prior Publication Data

US 2020/0181691 A1  Jun. 11, 2020

Related U.S. Application Data

(62) Division of application No. 15/601,545, filed on May 22, 2017, now Pat. No. 10,612,101.

(60) Provisional application No. 62/342,519, filed on May 27, 2016.

(51) Int. Cl.
| | | |
|---|---|---|
| *C12Q 1/68* | (2018.01) | |
| *C07H 21/04* | (2006.01) | |
| *C12Q 1/689* | (2018.01) | |
| *C12Q 1/686* | (2018.01) | |

(52) U.S. Cl.
CPC .............. *C12Q 1/689* (2013.01); *C12Q 1/686* (2013.01); *C12Q 2600/158* (2013.01); *C12Q 2600/16* (2013.01)

(58) Field of Classification Search
None
See application file for complete search history.

(56) References Cited

FOREIGN PATENT DOCUMENTS

| EP | 1862557 A1 * | 12/2007 | ............. C12Q 1/689 |
|---|---|---|---|
| WO | WO-2014060604 A2 * | 4/2014 | ............. A61B 18/22 |

* cited by examiner

*Primary Examiner* — Jeanine A Goldberg
(74) *Attorney, Agent, or Firm* — David J Chang

(57) ABSTRACT

Methods for the rapid detection of the presence or absence of *Mycoplasma genitalium* (MG) in a biological or non-biological sample are described. The methods can include performing an amplifying step, a hybridizing step, and a detecting step. Furthermore, primers, probes targeting the target MG gene, along with kits are provided that are designed for the detection of MG.

9 Claims, 4 Drawing Sheets

Specification includes a Sequence Listing.

SEQUENCE LISTING

<160> NUMBER OF SEQ ID NOS: 89

<210> SEQ ID NO 1
<211> LENGTH: 21
<212> TYPE: DNA
<213> ORGANISM: Artificial Sequence
<220> FEATURE:
<223> OTHER INFORMATION: 23s forward primer
<220> FEATURE:
<221> NAME/KEY: modified_base
<222> LOCATION: (21)..(21)
<223> OTHER INFORMATION: t-butylbenzyldA

<400> SEQUENCE: 1
ggggtggatc acctcctttc a                                              21

<210> SEQ ID NO 2
<211> LENGTH: 25
<212> TYPE: DNA
<213> ORGANISM: Artificial Sequence
<220> FEATURE:
<223> OTHER INFORMATION: 23s forward primer
<220> FEATURE:
<221> NAME/KEY: modified_base
<222> LOCATION: (25)..(25)

<223> OTHER INFORMATION: t-butylbenzyldC

<400> SEQUENCE: 2
caatgtttgg tctcacaact aacac                                              25

<210> SEQ ID NO 3
<211> LENGTH: 26
<212> TYPE: DNA
<213> ORGANISM: Artificial Sequence
<220> FEATURE:
<223> OTHER INFORMATION: 23s forward primer
<220> FEATURE:
<221> NAME/KEY: modified_base
<222> LOCATION: (26)..(26)
<223> OTHER INFORMATION: t-butylbenzyldA

<400> SEQUENCE: 3
tccagttctg aaagaatgtt tttgaa                                             26

<210> SEQ ID NO 4
<211> LENGTH: 26
<212> TYPE: DNA
<213> ORGANISM: Artificial Sequence
<220> FEATURE:
<223> OTHER INFORMATION: 23s forward primer
<220> FEATURE:
<221> NAME/KEY: modified_base
<222> LOCATION: (26)..(26)
<223> OTHER INFORMATION: t-butylbenzyldA

<400> SEQUENCE: 4
aaacgacaat ctttctagtt ccaaaa                                             26

<210> SEQ ID NO 5
<211> LENGTH: 23
<212> TYPE: DNA
<213> ORGANISM: Artificial Sequence
<220> FEATURE:
<223> OTHER INFORMATION: 23s forward primer
<220> FEATURE:
<221> NAME/KEY: modified_base
<222> LOCATION: (23)..(23)
<223> OTHER INFORMATION: t-butylbenzyldC

<400> SEQUENCE: 5
atgtttggtc tcacaactaa cac                                                23

<210> SEQ ID NO 6
<211> LENGTH: 24
<212> TYPE: DNA
<213> ORGANISM: Artificial Sequence
<220> FEATURE:
<223> OTHER INFORMATION: 23s forward primer
<220> FEATURE:
<221> NAME/KEY: modified_base
<222> LOCATION: (24)..(24)
<223> OTHER INFORMATION: t-butylbenzyldA

<400> SEQUENCE: 6
cagttctgaa agaatgtttt tgaa                                               24

<210> SEQ ID NO 7
<211> LENGTH: 23
<212> TYPE: DNA
<213> ORGANISM: Artificial Sequence
<220> FEATURE:
<223> OTHER INFORMATION: 23s forward primer
<220> FEATURE:
<221> NAME/KEY: modified_base

```
<222> LOCATION: (23)..(23)
<223> OTHER INFORMATION: t-butylbenzyldA

<400> SEQUENCE: 7
cgacaatctt tctagttcca aaa                                          23

<210> SEQ ID NO 8
<211> LENGTH: 24
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (24)..(24)
<223> OTHER INFORMATION: t-butylbenzyldC

<400> SEQUENCE: 8
cggatctcag gtttttacca cctc                                         24

<210> SEQ ID NO 9
<211> LENGTH: 20
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (20)..(20)
<223> OTHER INFORMATION: t-butylbenzyldA

<400> SEQUENCE: 9
cagattgctc cattcggaca                                              20

<210> SEQ ID NO 10
<211> LENGTH: 21
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (21)..(21)
<223> OTHER INFORMATION: t-butylbenzyldC

<400> SEQUENCE: 10
cagattgctc cattcggaca c                                            21

<210> SEQ ID NO 11
<211> LENGTH: 20
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (20)..(20)
<223> OTHER INFORMATION: t-butylbenzyldC

<400> SEQUENCE: 11
agattgctcc attcggacac                                              20

<210> SEQ ID NO 12
<211> LENGTH: 21
<212> TYPE: DNA
<213> ORGANISM: Artificial Sequence
<220> FEATURE:
<223> OTHER INFORMATION: 23s reverse primer
<220> FEATURE:
```

```
<221> NAME/KEY: modified_base
<222> LOCATION: (21)..(21)
<223> OTHER INFORMATION: t-butylbenzyldA

<400> SEQUENCE: 12
cacgtccttc atcgccttt a                                        21

<210> SEQ ID NO 13
<211> LENGTH: 22
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (22)..(22)
<223> OTHER INFORMATION: t-butylbenzyldC

<400> SEQUENCE: 13
gatctcaggt ttttaccacc tc                                      22

<210> SEQ ID NO 14
<211> LENGTH: 17
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (17)..(17)
<223> OTHER INFORMATION: t-butylbenzyldA

<400> SEQUENCE: 14
attgctccat tcggaca                                            17

<210> SEQ ID NO 15
<211> LENGTH: 18
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (18)..(18)
<223> OTHER INFORMATION: t-butylbenzyldC

<400> SEQUENCE: 15
attgctccat tcggacac                                           18

<210> SEQ ID NO 16
<211> LENGTH: 18
<212> TYPE: DNA
<213> ORGANISM: Artificial Sequence
<220> FEATURE:
<223> OTHER INFORMATION: 23s reverse primer
<220> FEATURE:
<221> NAME/KEY: modified_base
<222> LOCATION: (18)..(18)
<223> OTHER INFORMATION: t-butylbenzyldC

<400> SEQUENCE: 16
attgctccat tcggacac                                           18

<210> SEQ ID NO 17
<211> LENGTH: 19
<212> TYPE: DNA
<213> ORGANISM: Artificial Sequence
<220> FEATURE:
<223> OTHER INFORMATION: 23s reverse primer
```

```
<220> FEATURE:
<221> NAME/KEY: modified_base
<222> LOCATION: (19)..(19)
<223> OTHER INFORMATION: t-butylbenzyldA

<400> SEQUENCE: 17
cgtccttcat cgcctttta                                                       19

<210> SEQ ID NO 18
<211> LENGTH: 39
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 18
ggtcagtttg tatccagttc tgaaagaatg tttttgaac                                 39

<210> SEQ ID NO 19
<211> LENGTH: 39
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 19
gttcaaaaac attctttcag aactggatac aaactgacc                                 39

<210> SEQ ID NO 20
<211> LENGTH: 39
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 20
gaatgttttt gaacagttct ttcaaaactg aaaacgaca                                 39

<210> SEQ ID NO 21
<211> LENGTH: 40
<212> TYPE: DNA
```

```
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 21
tcagtttgta tccagttctg aaagaatgtt tttgaaccag                              40

<210> SEQ ID NO 22
<211> LENGTH: 40
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 22
tgttcaaaaa cattctttca gaactggata caaactgacc                              40

<210> SEQ ID NO 23
<211> LENGTH: 40
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 23
agaatgtttt tgaacagttc tttcaaaact gaaaacgaca                              40

<210> SEQ ID NO 24
<211> LENGTH: 30
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
```

```
<400> SEQUENCE: 24
ctaaaaggcg atgaaggacg tgttaacctg                                              30

<210> SEQ ID NO 25
<211> LENGTH: 30
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 25
ggtcagtttg tatccagttc tgaaagaatg                                              30

<210> SEQ ID NO 26
<211> LENGTH: 31
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 26
gttcaaaaac attctttcag aactggatac a                                            31

<210> SEQ ID NO 27
<211> LENGTH: 31
<212> TYPE: DNA
<213> ORGANISM: Artificial Sequence
<220> FEATURE:
<223> OTHER INFORMATION: 23s probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 27
gaatgttttt gaacagttct ttcaaaactg a                                            31

<210> SEQ ID NO 28
<211> LENGTH: 27
<212> TYPE: DNA
<213> ORGANISM: Artificial Sequence
<220> FEATURE:
<223> OTHER INFORMATION: 23s probe
<220> FEATURE:
```

```
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 28
ctaaaaggcg atgaaggacg tgttaac                                              27

<210> SEQ ID NO 29
<211> LENGTH: 27
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (27)..(27)
<223> OTHER INFORMATION: t-butylbenzyldC

<400> SEQUENCE: 29
gacttgaaac aataacaact tctcttc                                              27

<210> SEQ ID NO 30
<211> LENGTH: 28
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (28)..(28)
<223> OTHER INFORMATION: t-butylbenzyldA

<400> SEQUENCE: 30
gacttgaaac aataacaact tctcttca                                             28

<210> SEQ ID NO 31
<211> LENGTH: 28
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (28)..(28)
<223> OTHER INFORMATION: t-butylbenzyldA

<400> SEQUENCE: 31
aacaataaca acttctcttc actaaaga                                             28

<210> SEQ ID NO 32
<211> LENGTH: 29
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (29)..(29)
<223> OTHER INFORMATION: t-butylbenzyldA

<400> SEQUENCE: 32
caataacaac ttctcttcac taaagatta                                            29
```

```
<210> SEQ ID NO 33
<211> LENGTH: 26
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (26)..(26)
<223> OTHER INFORMATION: t-butylbenzyldA

<400> SEQUENCE: 33
accccttgga cttgaaacaa taacaa                                          26

<210> SEQ ID NO 34
<211> LENGTH: 22
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (22)..(22)
<223> OTHER INFORMATION: t-butylbenzyldA

<400> SEQUENCE: 34
agagaaccca ggatcatttg ga                                              22

<210> SEQ ID NO 35
<211> LENGTH: 20
<212> TYPE: DNA
<213> ORGANISM: Artificial Sequence
<220> FEATURE:
<223> OTHER INFORMATION: mgpB forward primer
<220> FEATURE:
<221> NAME/KEY: modified_base
<222> LOCATION: (20)..(20)
<223> OTHER INFORMATION: t-butylbenzyldA

<400> SEQUENCE: 35
ctggagagaa cccaggatca                                                 20

<210> SEQ ID NO 36
<211> LENGTH: 26
<212> TYPE: DNA
<213> ORGANISM: Artificial Sequence
<220> FEATURE:
<223> OTHER INFORMATION: mgpB reverse primer
<220> FEATURE:
<221> NAME/KEY: modified_base
<222> LOCATION: (26)..(26)
<223> OTHER INFORMATION: t-butylbenzyldA

<400> SEQUENCE: 36
gttgttatca taccttctga ttgcaa                                          26

<210> SEQ ID NO 37
<211> LENGTH: 25
<212> TYPE: DNA
<213> ORGANISM: Artificial Sequence
<220> FEATURE:
<223> OTHER INFORMATION: mgpB reverse primer
<220> FEATURE:
<221> NAME/KEY: modified_base
<222> LOCATION: (25)..(25)
<223> OTHER INFORMATION: t-butylbenzyldA

<400> SEQUENCE: 37
ctaccgttgt tatcatacct tctga                                           25
```

```
<210> SEQ ID NO 38
<211> LENGTH: 28
<212> TYPE: DNA
<213> ORGANISM: Artificial Sequence
<220> FEATURE:
<223> OTHER INFORMATION: mgpB reverse primer
<220> FEATURE:
<221> NAME/KEY: modified_base
<222> LOCATION: (28)..(28)
<223> OTHER INFORMATION: t-butylbenzyldA

<400> SEQUENCE: 38
catataaagc tctaccgttg ttatcata                                      28

<210> SEQ ID NO 39
<211> LENGTH: 28
<212> TYPE: DNA
<213> ORGANISM: Artificial Sequence
<220> FEATURE:
<223> OTHER INFORMATION: mgpB reverse primer
<220> FEATURE:
<221> NAME/KEY: modified_base
<222> LOCATION: (28)..(28)
<223> OTHER INFORMATION: t-butylbenzyldA

<400> SEQUENCE: 39
aatatcatat aaagctctac cgttgtta                                      28

<210> SEQ ID NO 40
<211> LENGTH: 32
<212> TYPE: DNA
<213> ORGANISM: Artificial Sequence
<220> FEATURE:
<223> OTHER INFORMATION: mgpB reverse primer
<220> FEATURE:
<221> NAME/KEY: modified_base
<222> LOCATION: (32)..(32)
<223> OTHER INFORMATION: t-butylbenzyldA

<400> SEQUENCE: 40
ttttccattt ttgctaagtt aatatcatat aa                                 32

<210> SEQ ID NO 41
<211> LENGTH: 26
<212> TYPE: DNA
<213> ORGANISM: Artificial Sequence
<220> FEATURE:
<223> OTHER INFORMATION: mgpB reverse primer
<220> FEATURE:
<221> NAME/KEY: modified_base
<222> LOCATION: (26)..(26)
<223> OTHER INFORMATION: t-butylbenzyldA

<400> SEQUENCE: 41
ggggttttcc atttttgcta agttaa                                        26

<210> SEQ ID NO 42
<211> LENGTH: 36
<212> TYPE: DNA
<213> ORGANISM: Artificial Sequence
<220> FEATURE:
<223> OTHER INFORMATION: mgpB probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
```

<222> LOCATION: (6)..(7)
<223> OTHER INFORMATION: BHQ-2

<400> SEQUENCE: 42
ggagagaacc caggatcatt tggattagta agaagc              36

<210> SEQ ID NO 43
<211> LENGTH: 41
<212> TYPE: DNA
<213> ORGANISM: Artificial Sequence
<220> FEATURE:
<223> OTHER INFORMATION: mgpB probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 43
aagattactg gagagaaccc aggatcattt ggattagtaa g              41

<210> SEQ ID NO 44
<211> LENGTH: 37
<212> TYPE: DNA
<213> ORGANISM: Artificial Sequence
<220> FEATURE:
<223> OTHER INFORMATION: mgpB probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 44
ctggagagaa cccaggatca tttggattag taagaag              37

<210> SEQ ID NO 45
<211> LENGTH: 37
<212> TYPE: DNA
<213> ORGANISM: Artificial Sequence
<220> FEATURE:
<223> OTHER INFORMATION: mgpB probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 45
cagcaaaact ttgcaatcag aaggtatgat aacaacg              37

<210> SEQ ID NO 46
<211> LENGTH: 37
<212> TYPE: DNA
<213> ORGANISM: Artificial Sequence
<220> FEATURE:

```
<223> OTHER INFORMATION: mgpB probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 46
cgttgttatc ataccttctg attgcaaagt tttgctg                                    37

<210> SEQ ID NO 47
<211> LENGTH: 20
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (20)..(20)
<223> OTHER INFORMATION: t-butylbenzyldA

<400> SEQUENCE: 47
tttctcccct gaatcggcaa                                                       20

<210> SEQ ID NO 48
<211> LENGTH: 20
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (20)..(20)
<223> OTHER INFORMATION: t-butylbenzyldA

<400> SEQUENCE: 48
caactccccc tcccctttcaa                                                      20

<210> SEQ ID NO 49
<211> LENGTH: 20
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (20)..(20)
<223> OTHER INFORMATION: t-butylbenzyldC

<400> SEQUENCE: 49 tcccctccc cttcaacttc                                                        20

<210> SEQ ID NO 50
<211> LENGTH: 28
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (28)..(28)
<223> OTHER INFORMATION: t-butylbenzyldC

<400> SEQUENCE: 50
atcccaattc agatgataat aaagtcac                                              28
```

<210> SEQ ID NO 51
<211> LENGTH: 27
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (27)..(27)
<223> OTHER INFORMATION: t-butylbenzyldA

<400> SEQUENCE: 51
atcccaattc agatgataat aaagtca                                27

<210> SEQ ID NO 52
<211> LENGTH: 21
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (21)..(21)
<223> OTHER INFORMATION: t-butylbenzyldA

<400> SEQUENCE: 52
tcccaccagt gactggatca a                                      21

<210> SEQ ID NO 53
<211> LENGTH: 20
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (20)..(20)
<223> OTHER INFORMATION: t-butylbenzyldC

<400> SEQUENCE: 53
caactcccac actgcttccc                                        20

<210> SEQ ID NO 54
<211> LENGTH: 23
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (23)..(23)
<223> OTHER INFORMATION: t-butylbenzyldC

<400> SEQUENCE: 54
tccaactccc acactgcttc ccc                                    23

<210> SEQ ID NO 55
<211> LENGTH: 21
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (21)..(21)
<223> OTHER INFORMATION: t-butylbenzyldC

<400> SEQUENCE: 55
tccaactccc acactgcttc c    21

<210> SEQ ID NO 56
<211> LENGTH: 19
<212> TYPE: DNA
<213> ORGANISM: Artificial Sequence
<220> FEATURE:
<223> OTHER INFORMATION: MgPar forward primer
<220> FEATURE:
<221> NAME/KEY: modified_base
<222> LOCATION: (19)..(19)
<223> OTHER INFORMATION: t-butylbenzyldC

<400> SEQUENCE: 56
caactcccac actgcttcc    19

<210> SEQ ID NO 57
<211> LENGTH: 26
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (26)..(26)
<223> OTHER INFORMATION: t-butylbenzyldA

<400> SEQUENCE: 57
ggtgaaaagt taggtataaa caccca    26

<210> SEQ ID NO 58
<211> LENGTH: 20
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (20)..(20)
<223> OTHER INFORMATION: t-butylbenzyldA

<400> SEQUENCE: 58
ctgctcctgt tcagatgtca    20

<210> SEQ ID NO 59
<211> LENGTH: 24
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (24)..(24)
<223> OTHER INFORMATION: t-butylbenzyldA

<400> SEQUENCE: 59
tgctcactat ccttgttaaa ttga    24

<210> SEQ ID NO 60
<211> LENGTH: 22
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (22)..(22)
<223> OTHER INFORMATION: t-butylbenzyldA

<400> SEQUENCE: 60 cacctccccca aacccaggta aa                                           22

<210> SEQ ID NO 61
<211> LENGTH: 21
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (21)..(21)
<223> OTHER INFORMATION: t-butylbenzyldA

<400> SEQUENCE: 61
acctccccaa acccaggtaa a                                             21

<210> SEQ ID NO 62
<211> LENGTH: 20
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (20)..(20)
<223> OTHER INFORMATION: t-butylbenzyldC

<400> SEQUENCE: 62
cctgctcccg ttcagatgtc                                               20

<210> SEQ ID NO 63
<211> LENGTH: 20
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (13)..(13)
<223> OTHER INFORMATION: 9-(aminoethoxy)-phenoxazine-2'-dC
<220> FEATURE:
<221> NAME/KEY: modified_base
<222> LOCATION: (20)..(20)
<223> OTHER INFORMATION: t-butylbenzyldC

<400> SEQUENCE: 63
cctgctcccg ttcaaatgtc                                               20

<210> SEQ ID NO 64
<211> LENGTH: 20
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (20)..(20)
<223> OTHER INFORMATION: t-butylbenzyldC

<400> SEQUENCE: 64
cctgctcccg ttcaratgtc                                               20

<210> SEQ ID NO 65
<211> LENGTH: 20
<212> TYPE: DNA
<213> ORGANISM: Artificial Sequence
<220> FEATURE:
<223> OTHER INFORMATION: MgPar reverse primer
<220> FEATURE:

<221> NAME/KEY: modified_base
<222> LOCATION: (20)..(20)
<223> OTHER INFORMATION: t-butylbenzyldC

<400> SEQUENCE: 65
cctgctcccg ttcaaatgtc                                          20

<210> SEQ ID NO 66
<211> LENGTH: 20
<212> TYPE: DNA
<213> ORGANISM: Artificial Sequence
<220> FEATURE:
<223> OTHER INFORMATION: MgPar reverse primer
<220> FEATURE:
<221> NAME/KEY: modified_base
<222> LOCATION: (20)..(20)
<223> OTHER INFORMATION: t-butylbenzyldC

<400> SEQUENCE: 66
cctgctcccg ttcagatgtc                                          20

<210> SEQ ID NO 67
<211> LENGTH: 40
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 67
ctccccactt tttctaacat caatgttggg gttaaatcaa                    40

<210> SEQ ID NO 68
<211> LENGTH: 40
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 68
ttgatttaac cccaacattg atgttagaaa aagtggggag                    40

<210> SEQ ID NO 69
<211> LENGTH: 34
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:

<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 69
cgcaatcaac tgttgctcag aagcttacta ggaa                              34

<210> SEQ ID NO 70
<211> LENGTH: 35
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 70
agttcctagt aagcttctga gcaacagttg attgc                             35

<210> SEQ ID NO 71
<211> LENGTH: 38
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 71
gatttaaccc caacattgat gttagaaaaa gtggggag                          38

<210> SEQ ID NO 72
<211> LENGTH: 38
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: modified_base
<222> LOCATION: (3)..(5)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (16)..(17)

```
<223> OTHER INFORMATION: propynyldU
<220> FEATURE:
<221> NAME/KEY: modified_base
<222> LOCATION: (20)..(20)
<223> OTHER INFORMATION: propynyldU
<220> FEATURE:
<221> NAME/KEY: modified_base
<222> LOCATION: (22)..(23)
<223> OTHER INFORMATION: propynyldU
<220> FEATURE:
<221> NAME/KEY: modified_base
<222> LOCATION: (32)..(32)
<223> OTHER INFORMATION: propynyldU

<400> SEQUENCE: 72
gatttaaccc caacattgat gttagaaaaa gtggggag                                38

<210> SEQ ID NO 73
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 73
atttaacccc aacattgatg ttagaaaaag tggggag                                 37

<210> SEQ ID NO 74
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: modified_base
<222> LOCATION: (2)..(4)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU
<220> FEATURE:
<221> NAME/KEY: modified_base
<222> LOCATION: (31)..(31)
<223> OTHER INFORMATION: propynyldU

<400> SEQUENCE: 74
```

-continued atttaacccc aacattgatg ttagaaaaag tggggag        37

<210> SEQ ID NO 75
<211> LENGTH: 38
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 75
gatttaaccc caacattgat gttagaaaaa gtggtgag        38

<210> SEQ ID NO 76
<211> LENGTH: 38
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (16)..(17)
<223> OTHER INFORMATION: propynyldU
<220> FEATURE:
<221> NAME/KEY: modified_base
<222> LOCATION: (20)..(20)
<223> OTHER INFORMATION: propynyldU
<220> FEATURE:
<221> NAME/KEY: modified_base
<222> LOCATION: (22)..(23)
<223> OTHER INFORMATION: propynyldU
<220> FEATURE:
<221> NAME/KEY: modified_base
<222> LOCATION: (32)..(32)
<223> OTHER INFORMATION: propynyldU

<400> SEQUENCE: 76
gatttaaccc caacattgat gttagaaaaa gtggtgag        38

<210> SEQ ID NO 77
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)

<223> OTHER INFORMATION: BHQ-2

<400> SEQUENCE: 77
atttaacccc aacattgatg ttagaaaaag tggtgag                                37

<210> SEQ ID NO 78
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU
<220> FEATURE:
<221> NAME/KEY: modified_base
<222> LOCATION: (31)..(31)
<223> OTHER INFORMATION: propynyldU

<400> SEQUENCE: 78
atttaacccc aacattgatg ttagaaaaag tggtgag                                37

<210> SEQ ID NO 79
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (32)..(32)
<223> OTHER INFORMATION: 7'deazadG

<400> SEQUENCE: 79
atttaacccc aacattgatg ttagaaaaag tggggag                                37

<210> SEQ ID NO 80
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature

```
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (33)..(33)
<223> OTHER INFORMATION: 7'deazadG

<400> SEQUENCE: 80
atttaacccc aacattgatg ttagaaaaag tggggag                               37

<210> SEQ ID NO 81
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (34)..(34)
<223> OTHER INFORMATION: 7'deazadG

<400> SEQUENCE: 81
atttaacccc aacattgatg ttagaaaaag tggggag                               37

<210> SEQ ID NO 82
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (35)..(35)
<223> OTHER INFORMATION: 7'deazadG

<400> SEQUENCE: 82
atttaacccc aacattgatg ttagaaaaag tggggag                               37

<210> SEQ ID NO 83
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
```

```
<220> FEATURE:
<221> NAME/KEY: misc_feature
<223> OTHER INFORMATION: 3' phosphate
<220> FEATURE:
<221> NAME/KEY: modified_base
<222> LOCATION: (2)..(4)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU
<220> FEATURE:
<221> NAME/KEY: modified_base
<222> LOCATION: (31)..(31)
<223> OTHER INFORMATION: propynyldU
<220> FEATURE:
<221> NAME/KEY: modified_base
<222> LOCATION: (32)..(32)
<223> OTHER INFORMATION: 7'deazadG

<400> SEQUENCE: 83 atttaaccccc aacattgatg ttagaaaaag tggggag                              37

<210> SEQ ID NO 84
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: modified_base
<222> LOCATION: (2)..(4)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU
<220> FEATURE:
<221> NAME/KEY: modified_base
<222> LOCATION: (31)..(31)
<223> OTHER INFORMATION: propynyldU
<220> FEATURE:
<221> NAME/KEY: modified_base
<222> LOCATION: (33)..(33)
<223> OTHER INFORMATION: 7'deazadG

<400> SEQUENCE: 84
```
atttaacccc aacattgatg ttagaaaaag tggggag          37

<210> SEQ ID NO 85
<211> LENGTH: 37
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: modified_base
<222> LOCATION: (2)..(4)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU
<220> FEATURE:
<221> NAME/KEY: modified_base
<222> LOCATION: (31)..(31)
<223> OTHER INFORMATION: propynyldU
<220> FEATURE:
<221> NAME/KEY: modified_base
<222> LOCATION: (34)..(34)
<223> OTHER INFORMATION: 7'deazadG

<400> SEQUENCE: 85
atttaacccc aacattgatg ttagaaaaag tggggag          37

<210> SEQ ID NO 86
<211> LENGTH: 34
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (33)..(33)
<223> OTHER INFORMATION: 7'deazadG

<400> SEQUENCE: 86
atttaacccc aacattgatg ttagaaaaag tggg          34

<210> SEQ ID NO 87
<211> LENGTH: 34
<212> TYPE: DNA

```
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 87
atttaacccc aacattgatg ttagaaaaag tggg                                  34

<210> SEQ ID NO 88
<211> LENGTH: 34
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: modified_base
<222> LOCATION: (2)..(4)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU

<400> SEQUENCE: 88
atttaacccc aacattgatg ttagaaaaag tggg                                  34

<210> SEQ ID NO 89
<211> LENGTH: 34
<212> TYPE: DNA
<213> ORGANISM: Artificial Sequence
<220> FEATURE:
<223> OTHER INFORMATION: MgPar probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: modified_base
<222> LOCATION: (2)..(4)
<223> OTHER INFORMATION: propynyldU
<220> FEATURE:
<221> NAME/KEY: misc_feature
<222> LOCATION: (6)..(7)
<223> OTHER INFORMATION: BHQ-2
<220> FEATURE:
<221> NAME/KEY: modified_base
```

```
<222> LOCATION: (8)..(8)
<223> OTHER INFORMATION: propynyldC
<220> FEATURE:
<221> NAME/KEY: modified_base
<222> LOCATION: (10)..(10)
<223> OTHER INFORMATION: propynyldC
<220> FEATURE:
<221> NAME/KEY: modified_base
<222> LOCATION: (13)..(13)
<223> OTHER INFORMATION: propynyldC
<220> FEATURE:
<221> NAME/KEY: modified_base
<222> LOCATION: (15)..(16)
<223> OTHER INFORMATION: propynyldU
<220> FEATURE:
<221> NAME/KEY: modified_base
<222> LOCATION: (19)..(19)
<223> OTHER INFORMATION: propynyldU
<220> FEATURE:
<221> NAME/KEY: modified_base
<222> LOCATION: (21)..(22)
<223> OTHER INFORMATION: propynyldU

<400> SEQUENCE: 89
atttaacccc aacattgatg ttagaaaaag tggg                             34
```

COMPOSITIONS AND METHODS FOR DETECTION OF *MYCOPLASMA GENITALIUM*

CROSS REFERENCE TO RELATED APPLICATIONS

This application is a divisional of U.S. patent application Ser. No. 15/601,545, filed May 22, 2017, which claims the benefit of priority of U.S. Provisional Patent Application Ser. No. 62/342,519, filed May 27, 2016, each of which is incorporated herein by reference in its entirety.

REFERENCE TO SEQUENCE LISTING

This application contains a Sequence Listing submitted as an electronic text file named "33594_US1_Sequence_Listing.txt", having a size in bytes of 30 kb, and created on Apr. 17, 2017. The information contained in this electronic file is hereby incorporated by reference in its entirety pursuant to 37 CFR § 1.52(e)(5).

FIELD OF THE INVENTION

The present disclosure relates to the field of molecular diagnostics, and more particularly to detection of *Mycoplasma genitalium*.

BACKGROUND OF THE INVENTION

*Mycoplasma genitalium* (MG) is a gram-negative bacterium that lacks a cell wall and lives on the surface and in the epithelial cells of the urinary and genital tracts of men and women. *M. genitalium* is a common cause of nongonococcal urethritis (NGU) in men and an increasingly recognized cause of cervicitis and pelvic inflammatory disease (PID) in women. A recent meta-analysis has shown that infection with *M. genitalium* was associated with an approximately two-fold increase in risk for cervicitis, pelvic inflammatory disease, preterm birth, spontaneous abortion, and infertility in women. The prevalence of *M. genitalium* in lower risk populations in both men and women has been reported to be approximately 1% to 3%. In higher risk populations, prevalence of 10% to 41% in men and 7.3% to 14% in women has been reported. The prevalence of *M. genitalium* in higher risk populations often exceeds that of *Neisseria gonorrhoeae* and is similar to the prevalence of *Chlamydia trachomatis*. *M. genitalium* infections largely go unrecognized, and infected individuals are either asymptomatic or have symptoms similar to those associated with other bacterial infections of the urogenital tract.

The diagnosis of *M. genitalium* infection has traditionally been culture of urogenital specimens but culture is insensitive and slow and may take up to 6 months to recover the organism. Nucleic acid amplification tests (NAATs) for the diagnosis of *M. genitalium* infection in the United States and Europe NAATs have been made available as Laboratory Developed Procedures (LDPs) and have been shown to have superior sensitivity compared to culture.

The Center for Disease Control (CDC) recommends that *M. genitalium* should be suspected in cases of persistent or recurrent urethritis and may be considered in persistent or recurrent cases of cervicitis and pelvic inflammatory disease (PID). The fact that *M. genitalium* is a slow-growing organism, culture is not readily available, slow and insensitive, NAATs are the preferred method for *M. genitalium* detection. In research settings, *M. genitalium* is diagnosed by NAAT testing of urine, urethral, vaginal, and cervical swabs and through endometrial biopsies, typically using in-house PCR or assays intended for research use only. Thus there is a need in the art for a quick and reliable method to specifically detect MG in a sensitive manner.

SUMMARY OF THE INVENTION

Certain embodiments in the present disclosure relate to methods for the rapid detection of the presence or absence of MG in a biological or non-biological sample, for example, multiplex detection of MG by real-time polymerase chain reaction in a single test tube. Embodiments include methods of detection of MG comprising performing at least one cycling step, which may include an amplifying step and a hybridizing step. Furthermore, embodiments include primers, probes, and kits that are designed for the detection of MG in a single tube. The detection methods are designed to target specific genes in the *M. genitalium* genome with a potential to discriminate against the nearest neighbor, *Mycoplasma* pneumonia, and also other pathogens or commensals found in the human mouth or urogenital tract.

A method for detecting MG in a sample is provided, including performing an amplifying step including contacting the sample with a set of primers designed to target a specific MG gene to produce an amplification product if MG is present in the sample; performing a hybridizing step including contacting the amplification product with one or more detectable probes to the target MG gene; and detecting the presence or absence of the amplified product, wherein the presence of the amplified product is indicative of the presence of MG in the sample and wherein the absence of the amplified product is indicative of the absence of MG in the sample; wherein the target MG gene is selected from the group consisting of the 23s ribosomal RNA (23s) gene, the conserved region A of the mgpB gene within the MgPa adhesion operon (mgpB), and the variable EF region of the mgpB partial repeats (MgPar). FIG. 1 shows a picture of the circular *M. genitalium* genome and locations of the mgpB gene and the nine MgPar partial repeats.

In one aspect a method of detecting *Mycoplasma genitalium* (MG) in a sample is provided, the method comprising performing an amplifying step comprising contacting the sample with a set of target MG gene primers to produce an amplification product if a target MG gene nucleic acid is present in the sample; performing a hybridizing step comprising contacting the amplification product with one or more detectable target MG gene probes; and detecting the presence or absence of the amplification product, wherein the presence of the amplification product is indicative of the presence of MG in the sample and wherein the absence of the amplification product is indicative of the absence of MG in the sample; wherein the set of target MG gene primers comprise a first primer comprising a first oligonucleotide sequence selected from the group consisting of SEQ ID NOs: 1-7, 29-35, and 47-56 or a complement thereof, and a second primer comprising a second oligonucleotide sequence selected from the group consisting of SEQ ID NOs: 8-17, 36-41, and 57-66, or a complement thereof; and wherein the one or more detectable target MG gene probes comprises a third oligonucleotide sequence selected from the group consisting of SEQ ID NOs: 18-28, 42-46, and 67-89, or the complement thereof.

In one embodiment, the primer set for amplification of the 23s gene target includes a first primer comprising or consisting of a first oligonucleotide sequence selected from the group consisting of SEQ ID NOs: 1, 2, 3, 4, 5, 6, and 7, or a complement thereof, and a second primer comprising or consisting of a second oligonucleotide sequence selected from the group consisting of SEQ ID NOs: 8, 9, 10, 11, 12, 13, 14, 15, 16, and 17, or a complement thereof, and the detectable probe for detection of the 23s gene amplification product includes or consists of the nucleic acid sequences of SEQ ID NOs: 18, 19, 20, 21, 22, 23, 24, 25, 26, 27, and 28, or a complement thereof.

In certain embodiments, the primer set for amplification of the 23s gene target includes a first primer comprising or consisting of a first oligonucleotide sequence selected from the group consisting of SEQ ID NOs: 3 and 4, or a complement thereof, and a second primer comprising or consisting of a second oligonucleotide sequence selected from the group consisting of SEQ ID NOs: 8 and 9, or a complement thereof, and the detectable probe for detection of the 23s gene amplification product includes or consists of the nucleic acid sequences of SEQ ID NO: 24, or a complement thereof.

In another embodiment, the primer set for amplification of the mgpB gene target includes a first primer comprising or consisting of a first oligonucleotide sequence selected from the group consisting of SEQ ID NOs: 29, 30, 31, 32, 33, 34, and 35, or a complement thereof, and a second primer comprising or consisting of a second oligonucleotide sequence selected from the group consisting of SEQ ID NOs: 36, 37, 38, 39, 40, and 41, or a complement thereof, and the detectable probe for detection of the mgpB gene amplification product includes or consists of the nucleic acid sequences of SEQ ID NOs: 42, 43, 44, 45, and 46, or a complement thereof.

In certain embodiments, the primer set for amplification of the mgpB gene target includes a first primer comprising or consisting of a first oligonucleotide sequence selected from the group consisting of SEQ ID NOs: 34 and 35, or a complement thereof, and a second primer comprising or consisting of a second oligonucleotide sequence selected from the group consisting of SEQ ID NOs: 40 and 41, or a complement thereof, and the detectable probe for detection of the mgpB gene amplification product includes or consists of the nucleic acid sequences of SEQ ID NOs: 45 and 46, or a complement thereof.

In another embodiment, the primer set for amplification of the MgPar gene target includes a first primer comprising or consisting of a first oligonucleotide sequence selected from the group consisting of SEQ ID NOs: 47, 48, 49, 50, 51, 52, 53, 54, 55, and 56, or a complement thereof, and a second primer comprising or consisting of a second oligonucleotide sequence selected from the group consisting of SEQ ID NOs: 57, 58, 59, 60, 61, 62, 63, 64, 65, and 66, or a complement thereof, and the detectable probe for detection of the MgPar gene amplification product includes or consists of the nucleic acid sequences of SEQ ID NOs: 67, 68, 69, 70, 71, 72, 73, 74, 75, 76, 77, 78, 79, 80, 81, 82, 83, 84, 85, 86, 87, 88, and 89, or a complement thereof.

In certain embodiments, the primer set for amplification of the MgPar gene target includes a first primer comprising or consisting of a first oligonucleotide sequence selected from the group consisting of SEQ ID NOs: 48 and 56, or a complement thereof, and a second primer comprising or consisting of a second oligonucleotide sequence selected from the group consisting of SEQ ID NOs: 65 and 66, or a complement thereof, and the detectable probe for detection of the MgPar gene amplification product includes or consists of the nucleic acid sequences of SEQ ID NOs: 80 and 89, or a complement thereof.

In some embodiments, the hybridizing step comprises contacting the amplification product with the detectable target MG gene probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the probe, wherein the presence or absence of fluorescence is indicative of the presence or absence of MG in the sample.

In some embodiments the amplifying and the hybridizing steps are repeated. Herein, the number of repetitions depends, e.g., on the nature of the sample. If the sample is a complex mixture of nucleic acids, more amplifying and hybridizing steps will be required to amplify the target sequence sufficient for detection. In some embodiments, the amplifying and the hybridizing steps are repeated at least about 20 times, but may be repeated as many as at least 25, 30, 40, 50, 60, or even 100 times. Further, detecting the presence or absence of the amplification product may be performed during or after each amplifying and hybridizing step, during or after every other amplifying and hybridizing step, during or after particular amplifying and hybridizing steps or during or after particular amplifying and hybridizing steps, in which—if present—sufficient amplification product for detection is expected. In some embodiments, the amplifying step employs a polymerase enzyme having 5' to 3' nuclease activity. In some embodiments, the donor fluorescent moiety and the corresponding acceptor moiety are within no more than 8-20 nucleotides of each other on the probe. In some embodiments, the acceptor moiety is a quencher.

In some embodiments the oligonucleotides comprise or consist of a sequence of nucleotides selected from SEQ ID NOs: 1-89, or a complement thereof have 100 or fewer nucleotides, 50 or fewer nucleotides, 40 or fewer nucleotides or 30 or fewer nucleotides. In some embodiments, the first and second target MG gene primers and detectable target MG gene probe have 40 or fewer nucleotides (e.g. 35 or fewer nucleotides, 30 or fewer nucleotides, etc.).

In another embodiment, the present disclosure provides an oligonucleotide that includes a nucleic acid having at least 70% sequence identity (e.g., at least 75%, 80%, 85%, 90% or 95%, etc.) to one of SEQ ID NOs: 1-89, or a complement thereof, which oligonucleotide has 100 or fewer nucleotides. Generally, these oligonucleotides may be primer nucleic acids, probe nucleic acids, or the like in these embodiments. In some embodiments, the oligonucleotides comprise at least one modified nucleotide, e.g., to alter nucleic acid hybridization stability relative to unmodified nucleotides. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. In some embodiments, at least one of the first and second target MG gene primers and detectable target MG gene probe comprises at least one modified nucleotide.

In some embodiments, amplification (the amplifying step) can employ a polymerase enzyme having 5' to 3' nuclease activity. Thus, the donor fluorescent moiety and the acceptor moiety, e.g., a quencher, may be within no more than 5 to 20 nucleotides (e.g., 8 or 10) of each other along the length of the probe. In another aspect, the detectable probe includes a nucleic acid sequence that permits secondary structure formation. Such secondary structure formation generally results in spatial proximity between the first and second fluorescent moiety. According to this method, the second fluorescent moiety on the probe can be a quencher.

The present disclosure provides for methods of detecting the presence or absence of MG in a biological sample from an individual. Such methods generally include performing at least one cycling step, which includes an amplifying step and a dye-binding step. Typically, the amplifying step includes contacting the sample with a plurality of pairs of primers designed to target a specific MG gene to produce one or more target MG gene amplification products if the target MG gene nucleic acid molecule is present in the sample, and the dye-binding step includes contacting the target MG gene amplification product with a double-stranded DNA binding dye. Such methods also include detecting the presence or absence of binding of the double-stranded DNA binding dye into the amplification product, wherein the presence of binding is indicative of the presence of MG in the sample, and wherein the absence of binding is indicative of the absence of MG in the sample. A representative double-stranded DNA binding dye is ethidium bromide. In addition, such methods also can include determining the melting temperature between the target MG gene amplification product and the double-stranded DNA binding dye, wherein the melting temperature confirms the presence or absence of MG. The target MG gene may include but is not limited to the 23s gene, the mgpB gene, and the MgPar partial repeats.

In another aspect, the methods of detecting MG in a biological sample from an individual is conducted together with methods to detect Trichomonas *vaginalis* (TV) from the same biological sample due to the asymptomatic nature of individuals infected with MG and/or TV. Primers, probes and kits used for detecting TV are described in U.S. Provisional Patent Application No. 62/342,600, titled "Compositions and methods for detection of Trichomonas *vaginalis*", which is incorporated herein by reference in its entirety. In one embodiment, the methods of detecting MG and TV in the biological sample are performed in the same reaction mixture as a multiplex assay.

In yet another aspect, a kit for detecting one or more nucleic acids of MG is provided. The kit can include one or more sets of primers specific for amplification of the target MG gene; and one or more detectable probes specific for detection of the target MG gene amplification products. The target MG gene may include but is not limited to the 23s gene, the mgpB gene, and the MgPar partial repeats.

In particular, the oligonucleotide primers and probes disclosed above in connection with the method according to the invention are suitable to being included in a kit according to the invention. Herein, a kit for detecting a nucleic acid of *Mycoplasma genitalium* (MG) in a sample is provided comprising a first primer comprising or consisting of a first oligonucleotide sequence selected from the group consisting of SEQ ID NOs: 1-7, 29-35, and 47-56 or a complement thereof; a second primer comprising or consisting of a second oligonucleotide sequence selected from the group consisting of SEQ ID NOs: 8-17, 36-41, and 57-66, or a complement thereof; and a fluorescently detectably labeled probe comprising or consisting of a third oligonucleotide sequence selected from the group consisting of SEQ ID NOs: 18-28, 42-46, and 67-89, or a complement, the detectably labeled probe configured to hybridize to an amplicon generated by the first primer and the second primer. In one aspect, the kit can include probes already labeled with donor and corresponding acceptor moiety, e.g., another fluorescent moiety or a dark quencher, or can include fluorophoric moieties for labeling the probes. The kit can also include at least one of nucleoside triphosphates, nucleic acid polymerase, and buffers necessary for the function of the nucleic acid polymerase. The kit can also include a package insert and instructions for using the primers, probes, and fluorophoric moieties to detect the presence or absence of MG in a sample. In some embodiments, the third detectably labeled oligonucleotide sequence comprises a donor fluorescent moiety and a corresponding acceptor moiety. In some embodiments, the acceptor moiety is a quencher. In some embodiments, at least one of the first, second, and third oligonucleotides comprises at least one modified nucleotide. In some embodiments, the first, second, and third oligonucleotides have 40 or fewer nucleotides.

In another aspect, compositions are provided comprising a set of oligonucleotide primers for amplifying a target MG gene as disclosed above. In some embodiments, the set of target MG gene primers comprises a first primer comprising a first oligonucleotide sequence selected from the group consisting of SEQ ID NOs: 1-7, 29-35, and 47-56 or a complement thereof, and a second primer comprising a second oligonucleotide sequence selected from the group consisting of SEQ ID NOs: 8-17, 36-41, and 57-66, or a complement thereof. In certain embodiments, the composition further comprises one or more detectable target MG gene probes comprising or consisting of a third oligonucleotide sequence selected from the group consisting of SEQ ID NOs: 18-28, 42-46, and 67-89, or the complement thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

[black], 100 [light grey] and 10 [grey] genomic equivalent concentrations per PCR reaction).

Figure 3:
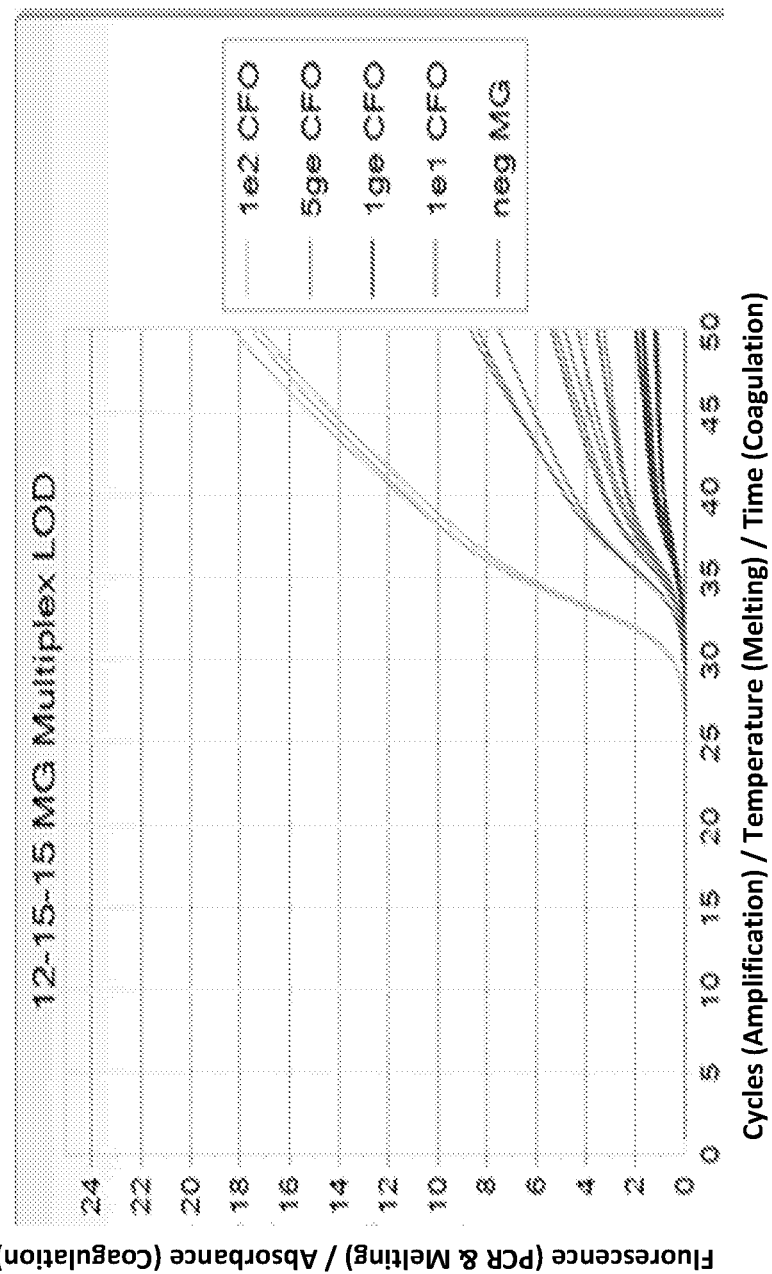

FIG. 3 shows PCR growth curves of a real-time PCR experiment with concentrations of genomic *M. genitalium* DNA template present in 100, 10, 5 and 1 genomic equivalent concentrations per PCR reaction (ge/PCR), in a co-amplification with internal control standard and Trichomonas *vaginalis* DNA template at 10 ge/PCR.

Figure 4:
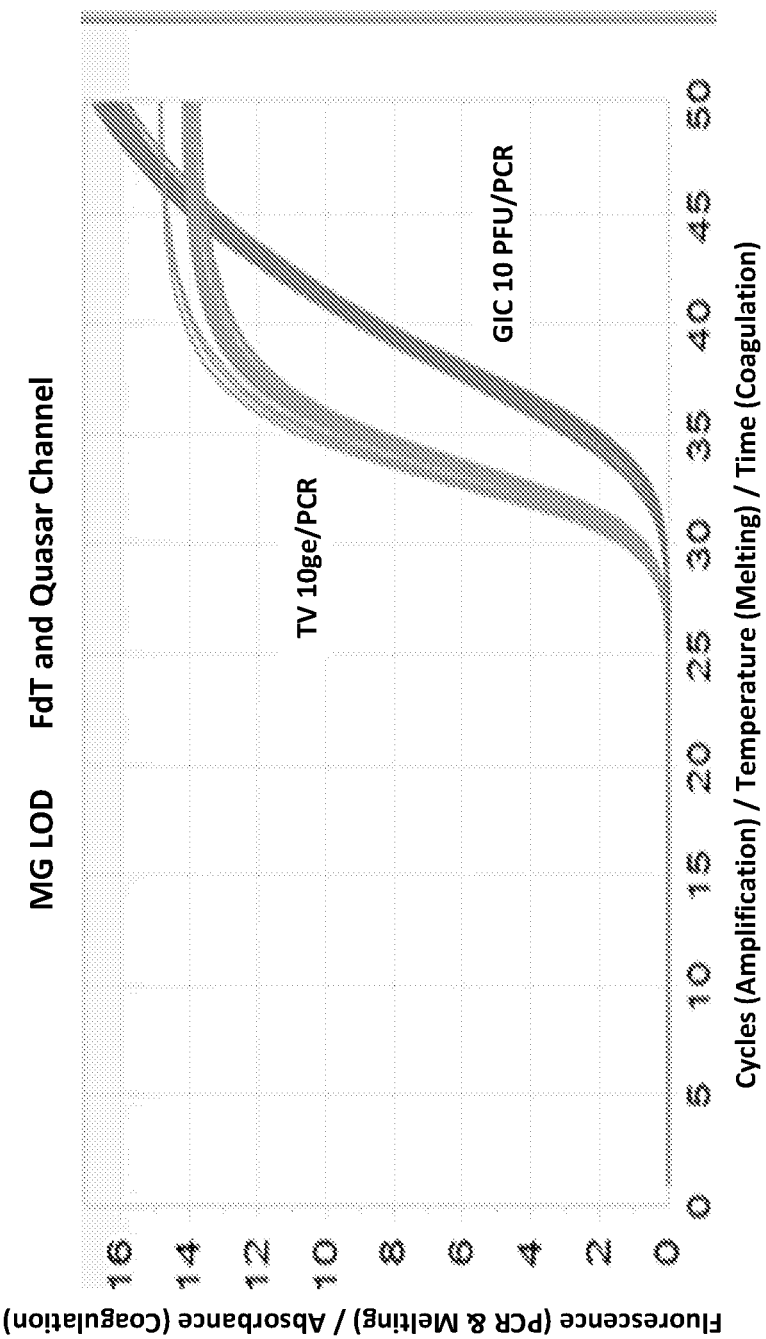

FIG. 4 shows PCR growth curves of the same real-time PCR experiment as shown in FIG. 3 with the amplification of the internal control standard and Trichomonas *vaginalis* DNA template at 10 ge/PCR.

DETAILED DESCRIPTION OF THE INVENTION

Diagnosis of MG infection by nucleic acid amplification provides a method for rapidly and accurately detecting the bacterial infection. A real-time assay for detecting MG in a sample is described herein. Primers and probes for detecting MG are provided, as are articles of manufacture or kits containing such primers and probes. The increased sensitivity of real-time PCR for detection of MG compared to other methods, as well as the improved features of real-time PCR including sample containment and real-time detection of the amplified product, make feasible the implementation of this technology for routine diagnosis of MG infections in the clinical laboratory.

The present disclosure includes oligonucleotide primers and fluorescent labeled hydrolysis probes that hybridize to a specific gene locus of the MG genome in order to specifically identify MG using TagMan® amplification and detection technology. Target selection for MG required a comprehensive search of the public sequence database, as well as literature search for MG targets with a potential to discriminate against the nearest neighbor, Mycloplasma pneumonia. Targets were selected for inclusivity purposes as well as for sensitivity purposes.

As a result of the analysis, possible target MG genes include the 23s ribosomal RNA gene (GenBank accession number NR077054), the conserved region A of the mgpB gene within the MgPa adhesion operon (mgpB, GenBank accession number FJ872586), and the variable EF region of the mgpB partial repeats (MgPar, GenBank accession number FJ872587). In certain aspects, a dual target approach may be implemented using the well conserved mgpB gene target. Herein, the well conserved region A of the mgpB gene may be selected for inclusivity purposes, and the variable EF region of the mgpB partial repeats multi-copy target may be selected for sensitivity purposes.

The disclosed methods may include performing at least one cycling step that includes amplifying one or more portions of the nucleic acid molecule gene target from a sample using one or more pairs of primers. "Primer(s)" as used herein refer to oligonucleotide primers that specifically anneal to the target gene in MG, and initiate DNA synthesis therefrom under appropriate conditions producing the respective amplification products. Each of the discussed primers anneals to a target within or adjacent to the respective target nucleic acid molecule such that at least a portion of each amplification product contains nucleic acid sequence corresponding to the target. The one or more amplification products are produced provided that one or more of the target MG gene nucleic acid is present in the sample, thus the presence of the one or more of target MG gene amplification products is indicative of the presence of MG in the sample. The amplification product should contain the nucleic acid sequences that are complementary to one or more detectable probes for target MG gene. "Probe(s)" as used herein refer to oligonucleotide probes that specifically anneal to nucleic acid sequence encoding the target MG gene. Each cycling step includes an amplification step, a hybridization step, and a detection step, in which the sample is contacted with the one or more detectable probes for detection of the presence or absence of MG in the sample.

As used herein, the term "amplifying" refers to the process of synthesizing nucleic acid molecules that are complementary to one or both strands of a template nucleic acid molecule. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus.* Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

Detection of MG

The present disclosure provides methods to detect MG by amplifying, for example, a portion of the target MG gene nucleic acid sequence. Nucleic acid sequences of the 23s ribosomal RNA gene, the mgpB gene and the MgPar partial repeats are publicly available (e.g., GenBank). Specifically, primers and probes to amplify and detect specific MG nucleic acid molecule targets are provided by the embodiments in the present disclosure.

For detection of MG, primers and probes to amplify the target MG gene are provided. Nucleic acids other than those exemplified herein can also be used to detect MG in a sample. For example, functional variants can be evaluated for specificity and/or sensitivity by those of skill in the art using routine methods. Representative functional variants can include, e.g., one or more deletions, insertions, and/or substitutions in the target MG gene nucleic acids disclosed herein.

More specifically, embodiments of the oligonucleotides each include a nucleic acid with a sequence selected from SEQ ID NOs: 1-89, a substantially identical variant thereof in which the variant has at least, e.g., 80%, 90%, or 95% sequence identity to one of SEQ ID NOs: 1-89, or a complement of SEQ ID NOs: 1-89 and the variant.

TABLE I

23s Forward Primers
Forward Primers

| Oligo Name | SEQ ID NO: | Sequence | Modifications |
|---|---|---|---|
| JH419BUA | 1 | GGGGTGGATCACCTCCTTTC<t_BB__dA> | t-butylbenzyldA |
| JH407BUC | 2 | CAATGTTTGGTCTCACAACTAACA<t_BB_dC> | t-butylbenzyldC |
| JH409BUA | 3 | TCCAGTTCTGAAAGAATGTTTTTGA<t_BB_dA> | t-butylbenzyldA |
| JH411BUA | 4 | AAACGACAATCTTTCTAGTTCCAAA<t_BB_dA> | t-butylbenzyldA |
| JH413BUC | 5 | ATGTTTGGTCTCACAACTAACA<t_BB_dC> | t-butylbenzyldC |
| JH415BUA | 6 | CAGTTCTGAAAGAATGTTTTTGA<t_BB_dA> | t-butylbenzyldA |
| JH417BUA | 7 | CGACAATCTTTCTAGTTCCAAA<t_BB_dA> | t-butylbenzyldA |

TABLE II

23s Reverse Primers
Reverse Primers

| Oligo Name | SEQ ID NO: | Sequence | Modifications |
|---|---|---|---|
| JH408BUC | 8 | CGGATCTCAGGTTTTTACCACCT<t_BB_dC> | t-butylbenzyldC |
| JH410BUA | 9 | CAGATTGCTCCATTCGGAC<_BB_dA> | t-butylbenzyldA |

TABLE II-continued

23s Reverse Primers
Reverse Primers

| Oligo Name | SEQ ID NO: | Sequence | Modifications |
|---|---|---|---|
| JH412BUC | 10 | CAGATTGCTCCATTCGGACA<t_BB_dC> | t-butylbenzyldC |
| JH414BUC | 11 | AGATTGCTCCATTCGGACA<t_BB_dC> | t-butylbenzyldC |
| JH416BUA | 12 | CACGTCCTTCATCGCCTTTT<t_BB_dA> | t-butylbenzyldA |
| JH418BUC | 13 | GATCTCAGGTTTTTACCACCT<t_BB_dC> | t-butylbenzyldC |
| JH420BUA | 14 | ATTGCTCCATTCGGAC<t_BB_dA> | t-butylbenzyldA |
| JH422BUC | 15 | ATTGCTCCATTCGGACA<t_BB_dC> | t-butylbenzyldC |
| JH424BUC | 16 | ATTGCTCCATTCGGACA<t_BB_dC> | t-butylbenzyldC |
| JH426BUA | 17 | CGTCCTTCATCGCCTTTT<t_BB_dA> | t-butylbenzyldA |

TABLE III

23s Probes
Probes

| Oligo Name | SEQ ID NO: | Sequence | Modifications |
|---|---|---|---|
| JH437HQ6 | 18 | <H>GGTCAG<Q>TTTGTATCCAGTTCTGAAAGAATGTTTTTGAAC<P> | P = phosphate, H = th-HEX, Q = BHQ2 |
| JH434HQ6 | 19 | <H>GTTCAA<Q>AAACATTCTTTCAGAACTGGATACAAACTGACC<P> | P = phosphate, H = th-HEX, Q = BHQ2 |
| JH439HQ6 | 20 | <H>GAATGT<Q>TTTTGAACAGTTCTTTCAAAACTGAAAACGACA<P> | P = phosphate, H = th-HEX, Q = BHQ2 |
| JH449HQ6 | 21 | <H>TCAGTT<Q>TGTATCCAGTTCTGAAAGAATGTTTTTGAACCAG<P> | P = phosphate, H = th-HEX, Q = BHQ2 |
| JH438HQ6 | 22 | <H>TGTTCA<Q>AAACATTCTTTCAGAACTGGATACAAACTGACC<P> | P = phosphate, H = th-HEX, Q = BHQ2, |
| JH451HQ6 | 23 | <H>AGAATG<Q>TTTTTGAACAGTTCTTTCAAAACTGAAAACGACA<P> | P = phosphate, H = th-HEX, Q = BHQ2 |
| JH441HQ6 | 24 | <H>CTAAAA<Q>GGCGATGAAGGACGTGTTAACCTG<P> | P = phosphate, H = th-HEX, Q = BHQ2 |
| JH443HQ6 | 25 | <H>GGTCAG<Q>TTTGTATCCAGTTCTGAAAGAATG<P> | P = phosphate, H = th-HEX, Q = BHQ2 |
| JH436HQ6 | 26 | <H>GTTCAA<Q>AAACATTCTTTCAGAACTGGATACA<P> | P = phosphate, H = th-HEX, Q = BHQ2 |
| JH445HQ6 | 27 | <H>GAATGT<Q>TTTTGAACAGTTCTTTCAAAACTGA<P> | P = phosphate, H = th-HEX, Q = BHQ2 |
| JH447HQ6 | 28 | <H>CTAAAA<Q>GGCGATGAAGGACGTGTTAAC<P> | P = phosphate, H = th-HEX, Q = BHQ2 |

TABLE IV mgpB Forward Primers
Forward Primers

| Oligo Name | SEQ ID NO: | Sequence | Modifications |
| --- | --- | --- | --- |
| JH311BUC | 29 | GACTTGAAACAATAACAACTTCTCTT<t_BB_dC> | t-butylbenzyldC |
| JH313BUA | 30 | GACTTGAAACAATAACAACTTCTCTTC<t_BB_dA> | t-butylbenzyldA |
| JH315BUA | 31 | AACAATAACAACTTCTCTTCACTAAAG<t_BB_dA> | t-butylbenzyldA |
| JH317BUA | 32 | CAATAACAACTTCTCTTCACTAAAGATT<t_BB_dA> | t-butylbenzyldA |
| JH319BUA | 33 | ACCCCTTGGACTTGAAACAATAACA<t_BB_dA> | t-butylbenzyldA |
| JH321BUA | 34 | AGAGAACCCAGGATCATTTGG<t_BB_dA> | t-butylbenzyldA |
| JH323BUA | 35 | CTGGAGAGAACCCAGGATC<t_BB_dA> | t-butylbenzyldA |

TABLE V mgpB Reverse Primers
Reverse Primers

| Oligo Name | SEQ ID NO: | Sequence | Modifications |
| --- | --- | --- | --- |
| JH310BUA | 36 | GTTGTTATCATACCTTCTGATTGCA<t_BB_dA> | t-butylbenzyldA |
| JH312BUA | 37 | CTACCGTTGTTATCATACCTTCTG<t_BB_dA> | t-butylbenzyldA |
| JH314BUA | 38 | CATATAAAGCTCTACCGTTGTTATCAT<t_BB_dA> | t-butylbenzyldA |
| JH316BUA | 39 | AATATCATATAAAGCTCTACCGTTGTT<t_BB_dA> | t-butylbenzyldA |
| JH320BUA | 40 | TTTTCCATTTTTGCTAAGTTAATATCATATA<t_BB_dA> | t-butylbenzyldA |
| JH322BUA | 41 | GGGGTTTTCCATTTTTGCTAAGTTA<t_BB_dA> | t-butylbenzyldA |

TABLE VI mgpB Probes
Probes

| Oligo Name | SEQ ID NO: | Sequence | Modifications |
| --- | --- | --- | --- |
| JH335HQ6 | 42 | <H>GGAGAG<Q>AACCCAGGATCATTTGGATTAGTAAGAAGC<P> | P = phosphate, H = th-HEX, Q = BHQ2 |
| JH337HQ6 | 43 | <H>AAGATT<Q>ACTGGAGAGAACCCAGGATCATTTGGATTAGTAAG<P> | P = phosphate, H = th-HEX, Q = BHQ2 |
| JH339HQ6 | 44 | <H>CTGGAG<Q>AGAACCCAGGATCATTTGGATTAGTAAGAAG<P> | P = phosphate, H = th-HEX, Q = BHQ2 |
| JH341HQ6 | 45 | <H>CAGCAA<Q>AACTTTGCAATCAGAAGGTATGATAACAACG<P> | P = phosphate, H = th-HEX, Q = BHQ2 |
| JH342HQ6 | 46 | <H>CGTTGT<Q>TATCATACCTTCTGATTGCAAAGTTTTGCTG<P> | P = phosphate, H = th-HEX, Q = BHQ2 |

TABLE VII

MgPar Forward Primers
Forward Primers

| Oligo Name | SEQ ID NO: | Sequence | Modifications |
| --- | --- | --- | --- |
| JH501BUA | 47 | TTTCTCCCCTGAATCGGCA<t_BB_dA> | t-butylbenzyldA |
| JH503BUA | 48 | CAACTCCCCCTCCCCTTCA<t_BB_dA> | t-butylbenzyldA |
| JH505BUC | 49 | TCCCCCTCCCCTTCAACTT<t_BB_dC> | t-butylbenzyldC |
| JH507BUC | 50 | ATCCCAATTCAGATGATAATAAAGT CA<t_BB_dC> | t-butylbenzyldC |
| JH509BUA | 51 | ATCCCAATTCAGATGATAATAAAGT C<t_BB_dA> | t-butylbenzyldA |
| JH511BUA | 52 | TCCCACCAGTGACTGGATCA<t_BB_dA> | t-butylbenzyldA |
| JLH531 | 53 | CAACTCCCACACTGCTTCC<t_BB_dC> | t-butylbenzyldC |
| KMMGP560F | 54 | TCCAACTCCCACACTGCTTCCC<t_BB_dC> | t-butylbenzyldC |
| KMMGP562F | 55 | TCCAACTCCCACACTGCTTC<t_BB_dC> | t-butylbenzyldC |
| KMMGP564F | 56 | CAACTCCCACACTGCTTC<t_BB_dC> | t-butylbenzyldC |

TABLE VIII

MgPar Reverse Primers
Reverse Primers

| Oligo Name | SEQ ID NO: | Sequence | Modifications |
| --- | --- | --- | --- |
| JH502BUA | 57 | GGTGAAAAGTTAGGTATAAACACC C<t_BB_dA> | t-butylbenzyldA |
| JH504BUA | 58 | CTGCTCCTGTTCAGATGTC<t_BB_dA> | t-butylbenzyldA |
| JH506BUA | 59 | TGCTCACTATCCTTGTTAAATTG<t_BB_dA> | t-butylbenzyldA |
| JH508BUA | 60 | CACCTCCCCAAACCCAGGTAA<t_BB_dA> | t-butylbenzyldA |
| JH510BUA | 61 | ACCTCCCCAAACCCAGGTAA<t_BB_dA> | t-butylbenzyldA |
| JLH536 | 62 | CCTGCTCCCGTTCAGATGT<t_BB_dC> | t-butylbenzyldC |
| JLH540 | 63 | CCTGCTCCCGTT<L>AAATGT<t_BB_dC> | t-butylbenzyldC, L = 9-(aminoethoxy)-phenoxazine-2'-dC |
| JLH538R | 64 | CCTGCTCCCGTTCA<R>ATGT<t_BB_dC> | t-butylbenzyldC R = A or G |
| JLH538R_A | 65 | CCTGCTCCCGTTCAAATGT<t_BB_dC> | t-butylbenzyldC |
| JLH538R_G | 66 | CCTGCTCCCGTTCAGATGT<t_BB_dC> | t-butylbenzyldC |

TABLE IX

MgPar Probes
Probes

| Oligo Name | SEQ ID NO: | Sequence | Modifications |
| --- | --- | --- | --- |
| JH521HQ6 | 67 | <H>CTCCCC<Q>ACTTTTTCTAACAT CAATGTTGGGGTTAAATCAA<P> | P = phosphate, H = th-HEX, Q = BHQ2 |
| JH522HQ6 | 68 | <H>TTGATT<Q>TAACCCCAACATT GATGTTAGAAAAAGTGGGGAG<P> | P = phosphate, H = th-HEX, Q = BHQ2 |
| JH523HQ6 | 69 | <H>CGCAAT<Q>CAACTGTTGCTCA GAAGCTTACTAGGAA<P> | P = phosphate, H = th-HEX, Q = BHQ2 |

TABLE IX-continued

MgPar Probes
Probes

| Oligo Name | SEQ ID NO: | Sequence | Modifications |
|---|---|---|---|
| JH524HQ6 | 70 | <H>AGTTCC<Q>TAGTAAGCTTCTG AGCAACAGTTGATTGC<P> | P = phosphate, H = th-HEX, Q = BHQ2 |
| JLH540HQ6 | 71 | <H>GATTTA<Q>ACCCCAACATTGA TGTTAGAAAAAGTGGGGAG<P> | P = phosphate, H = th-HEX, Q = BHQ2 |
| JLH540PDUHQ6 | 72 | <H>GA<U><U><U>A<Q>ACCCCAAC A<U><U>GA<U>G<U><U>AGAAAA AG<U>GGGGAG<P> | P = phosphate, H = th-HEX, Q = BHQ2, U = propynyldU |
| JLH544HQ6 | 73 | <H>ATTTAA<Q>CCCCAACATTGAT GTTAGAAAAAGTGGGGAG<P> | P = phosphate, H = th-HEX, Q = BHQ2 |
| JLH544PDUHQ6 | 74 | <H>A<U><U><U>AA<Q>CCCCAACA <U><U>GA<U>G<U><U>AGAAAAA G<U>GGGGAG<P> | P = phosphate, H = th-HEX, Q = BHQ2, U = propynyldU |
| JLH546HQ6 | 75 | <H>GATTTA<Q>ACCCCAACATTGA TGTTAGAAAAAGTGGTGAG<P> | P = phosphate, H = th-HEX, Q = BHQ2 |
| JLH546PDUHQ6 | 76 | <H>GATTTA<Q>ACCCCAACA <U><U>GA<U>G<U><U>AGAAAAAG<U> GGTGAG<P> | P = phosphate, H = th-HEX, Q = BHQ2, U = propynyldU |
| JLH548HQ6 | 77 | <H>ATTTAA<Q>CCCCAACATTGAT GTTAGAAAAAGTGGTGAG<P> | P = phosphate, H = th-HEX, Q = BHQ2 |
| JLH548PDUHQ6 | 78 | <H>ATTTAA<Q>CCCCAACA<U><U> GA<U>G<U><U>AGAAAAAG<U>GG TGAG<P> | P = phosphate, H = th-HEX, Q = BHQ2, U = propynyldU |
| JLH550HQ6 | 79 | <H>ATTTAA<Q>CCCCAACATTGAT GTTAGAAAAAGT<Y>GGGAG<P> | P = phosphate, H = th-HEX, Q = BHQ2, Y = 7'deazadG |
| JLH552HQ6 | 80 | <H>ATTTAA<Q>CCCCAACATTGAT GTTAGAAAAAGTG<Y>GGAG<P> | P = phosphate, H = th-HEX, Q = BHQ2, Y = 7'deazadG |
| JLH554HQ6 | 81 | <H>ATTTAA<Q>CCCCAACATTGAT GTTAGAAAAAGTGG<Y>GAG<P> | P = phosphate, H = th-HEX, Q = BHQ2, Y = 7'deazadG |
| JLH556HQ6 | 82 | <H>ATTTAA<Q>CCCCAACATTGAT GTTAGAAAAAGTGGG<Y>AG<P> | P = phosphate, H = th-HEX, Q = BHQ2, Y = 7'deazadG |
| JLH550PDUHQ6 | 83 | <H>A<U><U><U>AA<Q>CCCCAACA <U><U>GA<U>G<U><U>AGAAAAA G<U><Y>GGGAG<P> | P = phosphate, H = th-HEX, Q = BHQ2, U = propynyldU Y = 7'deazadG |
| JLH552PDUHQ6 | 84 | <H>A<U><U><U>AA<Q>CCCCAACA <U><U>GA<U>G<U><U>AGAAAAA G<U>G<Y>GGAG<P> | P = phosphate, H = th-HEX, Q = BHQ2, U = propynyldU Y = 7'deazadG |
| JLH554PDUHQ6 | 85 | <H>A<U><U><U>AA<Q>CCCCAACA <U><U>GA<U>G<U><U>AGAAAAA G<U>GG<Y>GAG<P> | P = phosphate, H = th-HEX, Q = BHQ2, U = propynyldU Y = 7'deazadG |
| JLH558HQ6 | 86 | <H>ATTTAA<Q>CCCCAACATTGAT GTTAGAAAAAGTG<Y>G<P> | P = phosphate, H = th-HEX, Q = BHQ2, Y = 7'deazadG |
| KMMGP560HQ6 | 87 | <H>ATTTAA<Q>CCCCAACATTGAT GTTAGAAAAAGTGGG<P> | P = phosphate, H = th-HEX, Q = BHQ2 |
| KMMGP562HQ6 | 88 | <H>A<U><U><U>AA<Q>CCCCAACA <U><U>GA<U>G<U><U>AGAAAAA GTGGG<P> | P = phosphate, H = th-HEX, Q = BHQ2, U = propynyldU |
| KMMGP564HQ6 | 89 | <H>A<U><U><U>AA<Q>C<X>C<X> AA<X>A<U><U>GA<U>G<U><U>AG AAAAAGTGGG<P> | P = phosphate, H = th-HEX, Q = BHQ2, U = propynyldU X = propynyldC |

In one embodiment, the above described sets of primers and probes are used in order to provide for detection of MG in a biological sample suspected of containing MG. The sets of primers and probes may comprise or consist of the primers and probes specific for the nucleic acid sequences of the 23s gene, mgpB gene, and the MgPar partial repeats comprising or consisting of the nucleic acid sequences of SEQ ID NOs: 1-89. In another embodiment, the primers and probes for the target MG genes comprise or consist of a functionally active variant of any of the primers and probes of SEQ ID NOs: 1-89.

A functionally active variant of any of the primers and/or probes of SEQ ID NOs: 1-89 may be identified by using the primers and/or probes in the disclosed methods. A functionally active variant of a primer and/or probe of any of the SEQ ID NOs: 1-89 pertains to a primer and/or probe which provides a similar or higher specificity and sensitivity in the described method or kit as compared to the respective sequence of SEQ ID NOs: 1-89.

The variant may, e.g., vary from the sequence of SEQ ID NOs: 1-89 by one or more nucleotide additions, deletions or substitutions such as one or more nucleotide additions, deletions or substitutions at the 5' end and/or the 3' end of the respective sequence of SEQ ID NOs: 1-89. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the target MG gene, e.g. the 23s gene, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of MG. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a target MG gene nucleic acid. A "probe" can be referred to as a "detection probe" meaning that it detects the target nucleic acid.

In some embodiments, the described target MG gene probes can be labeled with at least one fluorescent label. In one embodiment, the target MG gene probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs: 18-28, 42-46, and 67-89.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length. In some embodiments oligonucleotide primers are 40 or fewer nucleotides in length.

Constructs can include vectors each containing one of target MG gene primers and probes nucleic acid molecules. Constructs can be used, for example, as control template nucleic acid molecules. Vectors suitable for use are commercially available and/or produced by recombinant nucleic acid technology methods routine in the art. Target MG gene nucleic acid molecules can be obtained, for example, by chemical synthesis, direct cloning from MG, or by PCR amplification.

Constructs suitable for use in the methods typically include, in addition to the target MG gene nucleic acid molecules (e.g., a nucleic acid molecule that contains one or more sequences of SEQ ID NOs: 1-89), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing target MG gene nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described target MG gene nucleic acid sequences (e.g., SEQ ID NOs: 1-17, 29-41, and 47-66). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target MG gene nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ nucleic acid such as RNA or DNA (cDNA). The template nucleic acid need not be purified; it may be a minor fraction of a complex mixture, such as nucleic acid contained in human cells. Nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM MgCl$_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety and a corresponding quencher, which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced there between.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of MG

The present disclosure provides methods for detecting the presence or absence of MG in a biological or non-biological sample. Methods provided avoid problems of sample contamination, false negatives, and false positives. The methods include performing at least one cycling step that includes amplifying a portion of target nucleic acid molecules from a sample using one or more pairs of primers, and a FRET detecting step. Multiple cycling steps are performed, preferably in a thermocycler. Methods can be performed using the primers and probes to detect the presence of MG, and the detection of the target MG gene indicates the presence of MG in the sample.

As described herein, amplification products can be detected using labeled hybridization probes that take advantage of FRET technology. One FRET format utilizes TaqMan® technology to detect the presence or absence of an amplification product, and hence, the presence or absence of MG. TagMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of MG in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler® Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of MG genomes). If amplification of target nucleic acid occurs and an amplification product is produced, the step of hybridizing results in a detectable signal based upon FRET between the members of the pair of probes.

Generally, the presence of FRET indicates the presence of MG in the sample, and the absence of FRET indicates the absence of MG in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of a MG infection.

Representative biological samples that can be used in practicing the methods include, but are not limited to respiratory specimens, fecal specimens, blood specimens, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release MG nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the probes from the amplification products can confirm the presence or absence of MG in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present disclosure are not limited by the configuration of one or more commercially available instruments.

Articles of Manufacture/Kits

Embodiments of the present disclosure further provide for articles of manufacture, compositions or kits to detect MG. An article of manufacture can include primers and probes used to detect the target MG gene, together with suitable packaging materials. Compositions can include primers used to amplify the target MG gene. In certain embodiments compositions can also comprise probes for detecting the target MG gene. Representative primers and probes for detection of MG are capable of hybridizing to target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the probes. Examples of suitable FRET donor fluorescent moieties and corresponding acceptor fluorescent moieties are provided above.

Articles of manufacture can also contain a package insert or package label having instructions thereon for using the primers and probes to detect MG in a sample. Articles of manufacture and compositions may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples, tables and figures are provided to aid the understanding of the subject matter, the true scope of which is set forth in the appended claims. It is understood that modifications can be made in the procedures set forth without departing from the spirit of the invention.

Example I

Target selection for MG was the result of a comprehensive search of the public sequence database. Multiple methods were used to search for *Mycoplasma genitalium* sequences and its nearest neighbor, *Mycoplasma pneumoniae*, to design for assay exclusivity. The MG targets selected had the most coverage in the public database (mgpB 120 sequences, MgPar 5 whole genome assemblies). MG has a small compact genome, which limited regions to target for NAT design. The mgpB surface protein gene (called the MgPar target) was selected for the assay due to its multi-copy number. Surface proteins are known to undergo recombination, which can result in a failed assay. To mitigate the associated risks, a dual target approach was implemented using a well conserved target (called the mgpB target).

Figure 1:
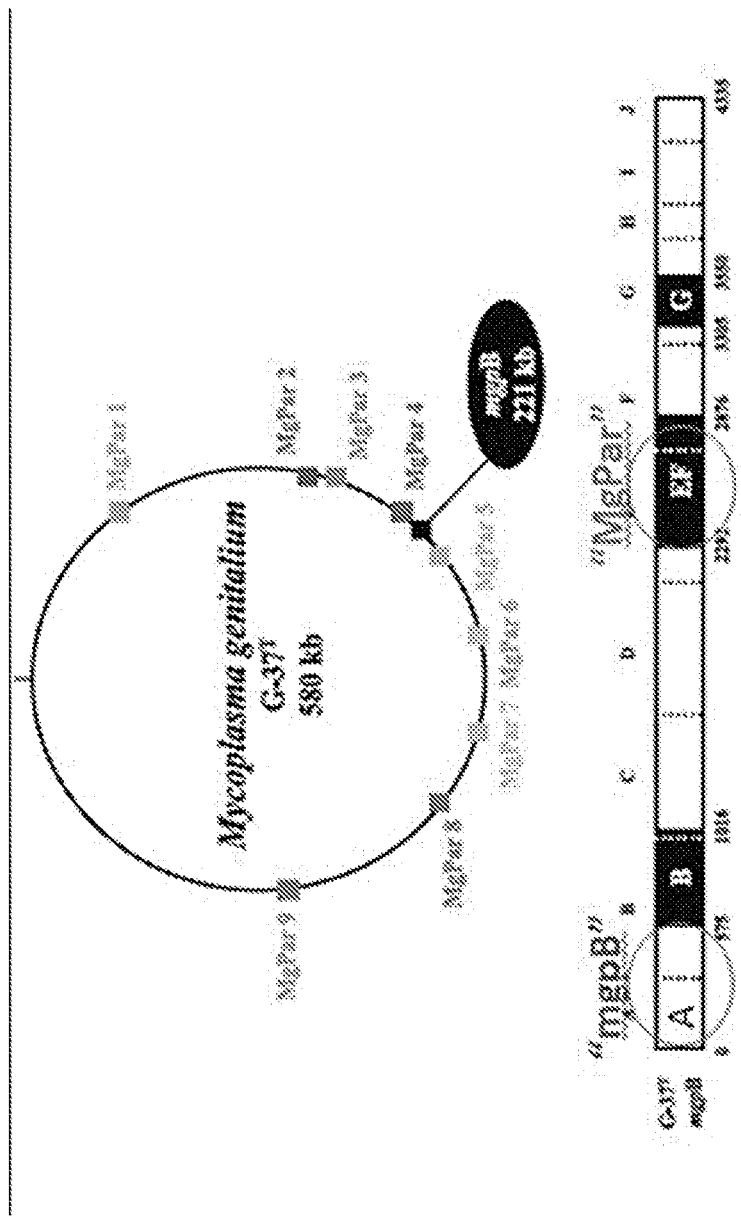
FIG. 1 is a graphical representation of the *M. genitalium* strain G37 genome with the locations of the mgpB gene and the MgPar partial repeats being shown.

The MgPa operon codes three genes: mgpA, mgpB and mgpC (black circle labeled as mgpB 221 kb in FIG. 1). mgpB (4335 bp) is present in the complete operon but there are nine partial repeats (MgPar's) outside of the operon. The repeats are partial copies of mgpB (FIG. 1). The well conserved region A of the mgpB gene (called the mgpB target) was selected for inclusivity purposes, and the variable region EF (called the MgPar target) multi-copy target was selected for sensitivity purposes (FIG. 1).

Real-time PCR detection of MG were performed using either the Cobas® 4800 system or the Cobas® 6800/8800 systems platforms (Roche Molecular Systems, Inc., Pleasanton, Calif.). The final concentrations of the amplification reagents are shown below:

TABLE X

| PCR Amplification Reagents | |
|---|---|
| Master Mix Component | Final Conc (50 uL) |
| DMSO | 0-5.4 % |
| NaN3 | 0.027-0.030 % |
| Potassium acetate | 120.0 mM |
| Glycerol | 3.0 % |
| Tween 20 | 0.02 % |
| EDTA | 0-43.9 uM |
| Tricine | 60.0 mM |
| Aptamer | 0.18-0.22 uM |
| UNG Enzyme | 5.0-10.0 U |
| Z05-SP-PZ Polymerase | 30.0-45.0 U |
| dATP | 400.0-521.70 uM |
| dCTP | 400.0-521.70 uM |
| dGTP | 400.0-521.70 uM |
| dUTP | 800.0-1043.40 uM |
| Forward primer oligonucleotides | 0.15-0.50 μM |
| Reverse primer oligonucleotides | 0.15-0.50 μM |
| Probe oligonucleotides | 0.10 μM |
| Manganese Acetate | 3.30-3.80 mM |

The following table shows the typical thermoprofile used for PCR amplification reaction:

TABLE XVII

| | | | | | | |
|---|---|---|---|---|---|---|
| | | PCR Thermoprofile | | | | |
| Program Name | Target (° C.) | Acquisition Mode | Hold (hh:mm:ss) | Ramp Rate (° C./s) | Cycles | Analysis Mode |
| Pre-PCR | 50 | None | 00:02:00 | 4.4 | 1 | None |
| | 94 | None | 00:00:05 | 4.4 | | |
| | 55 | None | 00:02:00 | 2.2 | | |
| | 60 | None | 00:06:00 | 4.4 | | |
| | 65 | None | 00:04:00 | 4.4 | | |
| 1st Measurement | 95 | None | 00:00:05 | 4.4 | 5 | Quantification |
| | 55 | Single | 00:00:30 | 2.2 | | |
| 2nd Measurment | 91 | None | 00:00:05 | 4.4 | 45 | Quantification |
| | 58 | Single | 00:00:25 | 2.2 | | |
| Cooling | 40 | None | 00:02:00 | 2.2 | 1 | None |

Figure 2:
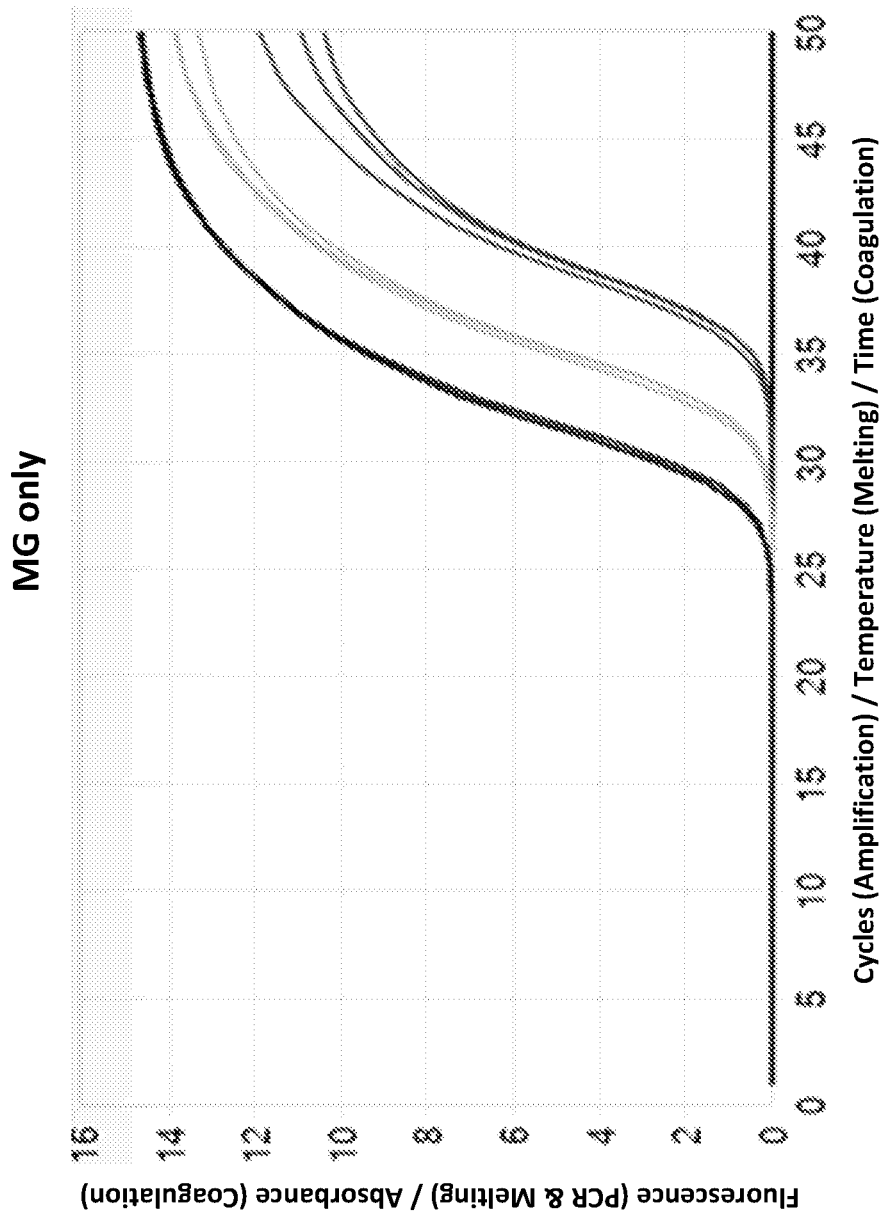
FIG. 2 shows PCR growth curves of a real-time PCR experiment in the presence of various concentrations of genomic *M. genitalium* DNA template (present in 1000

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C. FIG. 2 depicts a typical amplification experiment where PCR growth curves are shown in various concentrations of genomic MG template DNA.

The amplification and detection of the target MG genes, 23s rRNA, mgpB, and MgPar were performed using the conditions described above. The results of the experiments using several selected oligonucleotide primers and probes against genomic MG DNA present at a concentration of 1000 genomic equivalent/PCR are shown below as Ct values (threshold cycle) for the amplification reactions.

TABLE XVIII

Amplification and Detection of target MG genes

| Target MG Gene | Forward primer SEQ ID NO | Reverse primer SEQ ID NO | Probe SEQ ID NO | Ct values 1000 ge/ PCR of MG |
|---|---|---|---|---|
| 23s rRNA | 3 | 8 | 24 | 28.0 |
| | 3 | 9 | 24 | 28.1 |
| | 4 | 8 | 24 | 27.3 |
| | 4 | 9 | 24 | 28.3 |
| mgpB | 34 | 40 | 45 | 27.9 |
| | 35 | 41 | 45 | 27.5 |
| | 34 | 40 | 46 | 27.2 |
| | 35 | 41 | 46 | 27.5 |
| MgPar | 48 | 66 | 80 | 28.2 |
| | 56 | 65 | 80 | 32.4 |
| | 48 | 66 | 89 | 28.7 |
| | 56 | 65 | 89 | 33.1 |

Example 2

The amplification and detection of the MG mgpB and the MG MgPar genes was performed as described in Example 1 with the exception that genomic template DNA for Trichomonas vaginalis (TV) was included in the PCR assay together with primers and probes that can amplify and detect TV. In this experiment, primers and probes, disclosed in U.S. Provisional Application No. 62/342,600, that hybridize to the 5.8s rRNA gene were used.

MG Limit of Detection (LOD) was tested at 100, 10, 5 and 1 genomic equivalent concentrations per PCR reaction (ge/PCR), in a co-amplification with internal control standard and TV at 10 ge/PCR. The results are shown on FIGS. 3 and 4. All levels of MG were detected with no dropouts, and MG LOD was determined to be <1 ge/PCR.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of detecting *Mycoplasma genitalium* (MG) in a sample, the method comprising:

performing an amplifying step by the polymerase chain reaction (PCR) comprising contacting the sample with a set of target MG gene primers to produce an amplification product if a target MG gene nucleic acid is present in the sample;

performing a hybridizing step comprising contacting the amplification product with one or more detectable target MG gene probes; and detecting the presence or absence of the amplification product, wherein the presence of the amplification product is indicative of the presence of MG in the sample and wherein the absence of the amplification product is indicative of the absence of MG in the sample;

wherein the set of target MG gene primers and the one or more detectable target MG gene probes amplify and detect region A of the mgpB gene (mgpB); and wherein the set of target MG gene primers comprise a forward primer consisting of a first oligonucleotide sequence selected from the group consisting of SEQ ID NOs: 34-35, and a reverse primer consisting of a second oligonucleotide sequence selected from the group consisting of SEQ ID NOs: 40-41;

wherein the one or more detectable target MG gene probes consists of a third oligonucleotide sequence selected from the group consisting of SEQ ID NOs: 45-46; and wherein the limit of detection (LoD) of MG in the sample is less than 10 genomic equivalents per PCR reaction (ge/PCR).

2. The method of claim 1, wherein:

the hybridizing step comprises contacting the amplification product with the detectable target MG gene probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the probe, wherein the presence or absence of fluorescence is indicative of the presence or absence of MG in the sample.

3. The method of claim 2, wherein said amplifying step employs a polymerase enzyme having 5' to 3' nuclease activity.

4. The method of claim 2, wherein the donor fluorescent moiety and the corresponding acceptor moiety are within no more than 8-20 nucleotides of each other on the probe.

5. The method of claim 2, wherein the acceptor moiety is a quencher.

6. The method of claim 1, wherein the first oligonucleotide sequence consists of SEQ ID NO: 34, the second oligonucleotide sequence consists of SEQ ID NO: 40, and the third oligonucleotide sequence consists of SEQ ID NO: 45.

7. The method of claim 1, wherein the first oligonucleotide sequence consists of SEQ ID NO: 35, the second oligonucleotide sequence consists of SEQ ID NO: 41, and the third oligonucleotide sequence consists of SEQ ID NO: 45.

8. The method of claim 1, wherein the first oligonucleotide sequence consists of SEQ ID NO: 34, the second oligonucleotide sequence consists of SEQ ID NO: 40, and the third oligonucleotide sequence consists of SEQ ID NO: 46.

9. The method of claim 1, wherein the first oligonucleotide sequence consists of SEQ ID NO: 35, the second oligonucleotide sequence consists of SEQ ID NO: 41, and the third oligonucleotide sequence consists of SEQ ID NO: 46.

* * * * *